(12) United States Patent
Ortyn et al.

(10) Patent No.: US 6,580,504 B1
(45) Date of Patent: Jun. 17, 2003

(54) MULTIPASS CAVITY FOR ILLUMINATION AND EXCITATION OF MOVING OBJECTS

(75) Inventors: William E. Ortyn, Bainbridge Island, WA (US); David A. Basiji, Seattle, WA (US); Keith L. Frost, Seattle, WA (US); N. Robert McRuer, Mercer Island, WA (US)

(73) Assignee: Amnis Corporation, Seattle, WA (US)

( * ) Notice: Subject to any disclaimer, the term of this patent is extended or adjusted under 35 U.S.C. 154(b) by 0 days.

(21) Appl. No.: 09/689,172

(22) Filed: Oct. 12, 2000

Related U.S. Application Data

(63) Continuation-in-part of application No. 09/490,478, filed on Jan. 24, 2000, now Pat. No. 6,249,341
(60) Provisional application No. 60/117,203, filed on Jan. 25, 1999.

(51) Int. Cl.⁷ .............................................. G01N 21/00
(52) U.S. Cl. ...................... 356/338; 356/337; 356/246
(58) Field of Search ........................... 356/72, 73, 410, 356/440, 246, 338, 336, 337, 339, 340, 342, 343

(56) References Cited

U.S. PATENT DOCUMENTS 3,518,001 A * 6/1970 Hell ............................ 356/315
3,572,946 A * 3/1971 Little ........................... 356/413

(List continued on next page.)

FOREIGN PATENT DOCUMENTS

WO   WO 00/42412   7/2000   .......... G01N/15/02

OTHER PUBLICATIONS

Ong, S.–H.; Horne, D.; Yeung, C.–K.; Nickolls, P.; Cole, T. "Development of an Imaging Flow Cytometer." Analytical and Quantitative Cytology and Histology. XIVth International Conference on Medical and Biological Engineering and the VIIth International Conference on Medical Physics, Espoo, Finland. Aug. 11–15, 1985, pp. 375–382.

Ong, Sim Heng. "Development of a System for Imaging and Classifying Biological Cells in a Flow Cytometer." Doctor of Philosophy Thesis. University of Sydney, School of Electrical Engineering. Aug. 1985.

*Primary Examiner*—Frank G. Font
*Assistant Examiner*—Roy M. Punnoose
(74) *Attorney, Agent, or Firm*—Ronald M. Anderson

(57) ABSTRACT

An illumination system for increasing a light signal from an object passing through a reflection cavity. The reflection cavity is disposed between spaced-apart, opposed first and second surfaces disposed on opposite sides of a moving stream of objects. A light collection system is disposed substantially orthogonal to a plane passing through the surfaces and the stream so as to collect light that is scattered from or emitted by the objects as they pass through a field of view disposed between the first and second surfaces. A beam of light from a laser source is directed through the stream of moving objects in a direction nearly orthogonal to the stream (but slightly inclined) and lying in the plane that extends through the surfaces and the stream. Due to the reflection angle and the distance between the stream and the first surface, the point at which the light reflected from the first surface intersects the stream on a second pass is displaced from where it passed though the stream on its initial pass. The light is reflected back and forth between the surfaces a plurality of times, illuminating a different portion of the field of view with each pass until, having ranged over the field of view, the light exits the reflection cavity. The "recycling" of the light beam in this manner substantially improves the SNR of the detection system by increasing an average illumination intensity experienced by the objects in the stream.

18 Claims, 11 Drawing Sheets

U.S. PATENT DOCUMENTS

| | | | |
|---|---|---|---|
| 4,311,387 A | * 1/1982 | deMey et al. | 356/318 |
| 4,786,165 A | 11/1988 | Yamamoto et al. | 356/23 |
| 4,906,094 A | 3/1990 | Ashida | 356/336 |
| 5,159,397 A | 10/1992 | Kosaka et al. | 356/73 |
| 5,159,398 A | 10/1992 | Maekawa et al. | 356/73 |
| 5,159,642 A | 10/1992 | Kosaka | 382/6 |
| 5,247,339 A | 9/1993 | Ogino | 356/73 |
| 5,272,354 A | 12/1993 | Kosaka | 250/574 |
| 5,273,633 A | * 12/1993 | Wang | 356/344 |
| 5,422,712 A | 6/1995 | Ogino | 356/73 |
| 5,444,527 A | 8/1995 | Kosaka | 356/73 |
| 5,471,294 A | 11/1995 | Ogino | 356/73 |
| 5,485,276 A | * 1/1996 | Bien et al. | 356/437 |
| 5,548,395 A | 8/1996 | Kosaka | 356/73 |
| 5,596,401 A | 1/1997 | Kusuzawa | 356/23 |
| 5,633,503 A | 5/1997 | Kosaka | 250/458.1 |
| 5,644,388 A | 7/1997 | Maekawa et al. | 356/73 |
| 5,644,402 A | * 7/1997 | Chevallet | 356/440 |
| 5,760,899 A | 6/1998 | Eismann | 356/326 |
| 5,766,957 A | * 6/1998 | Robinson et al. | 356/440 |
| RE35,868 E | 8/1998 | Kosaka | 250/574 |
| 5,831,723 A | 11/1998 | Kubota et al. | 356/73 |
| 5,854,685 A | * 12/1998 | Levine | 356/440 |

* cited by examiner

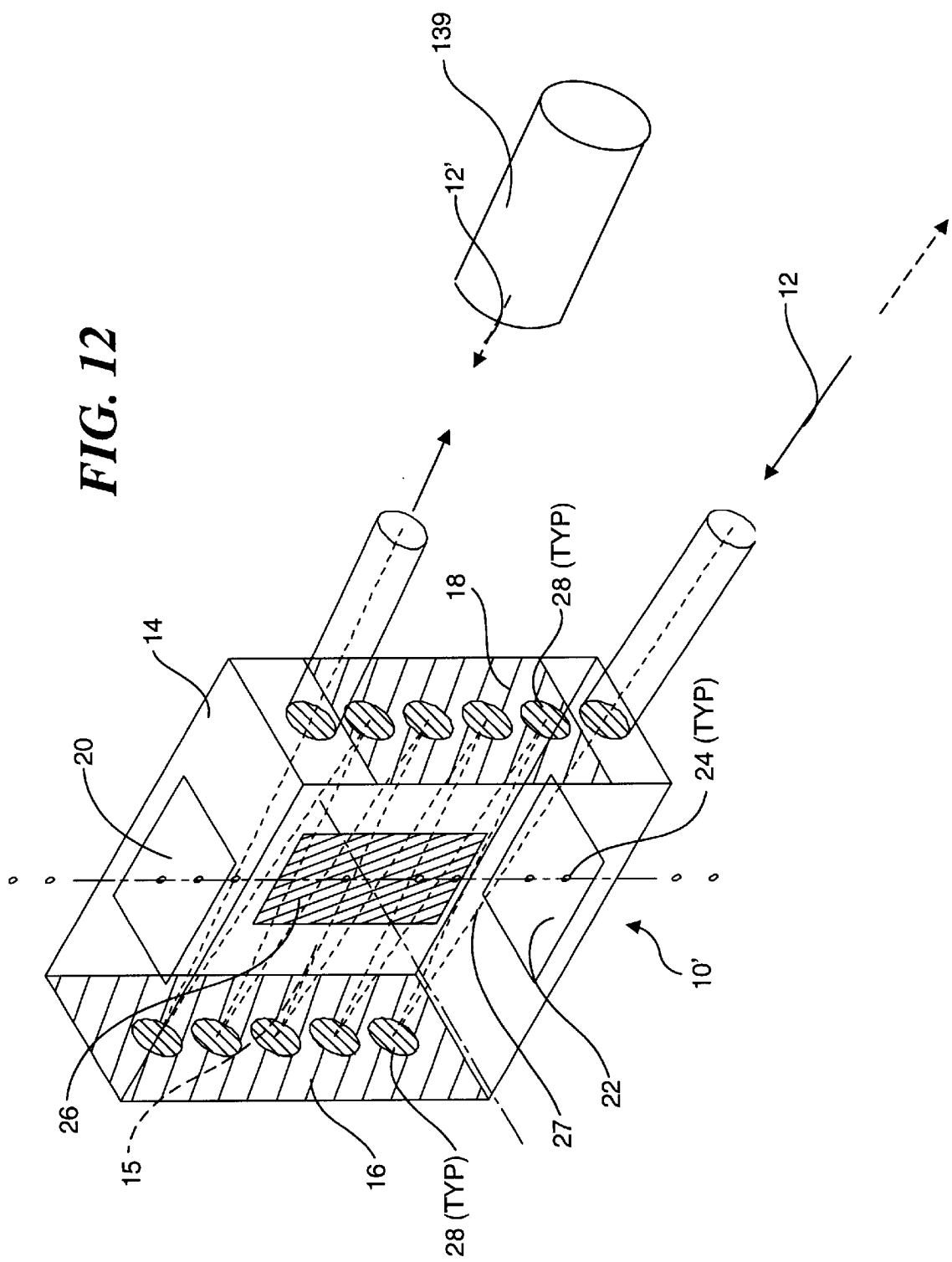

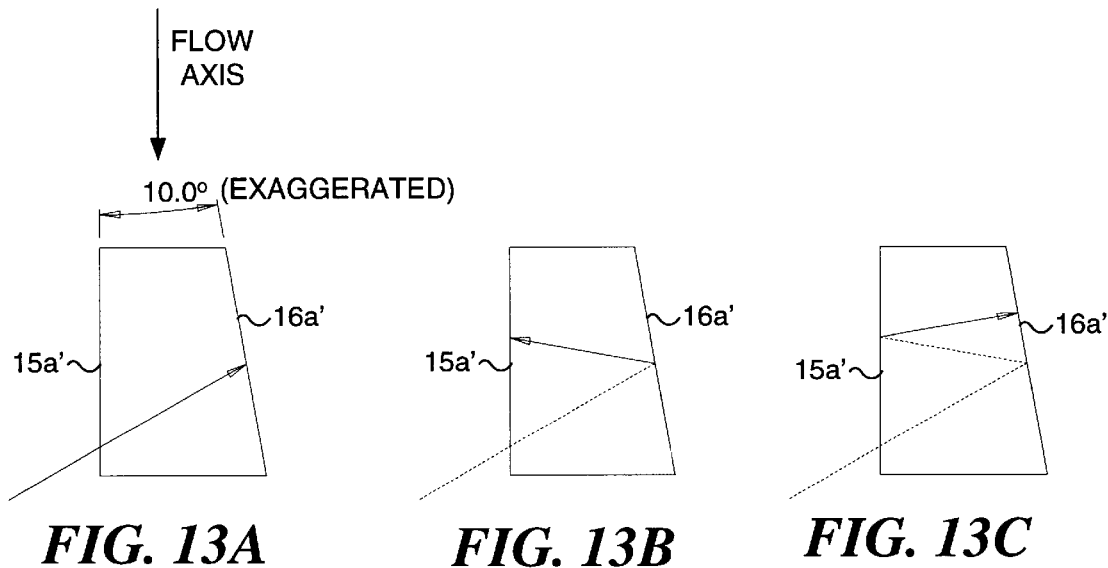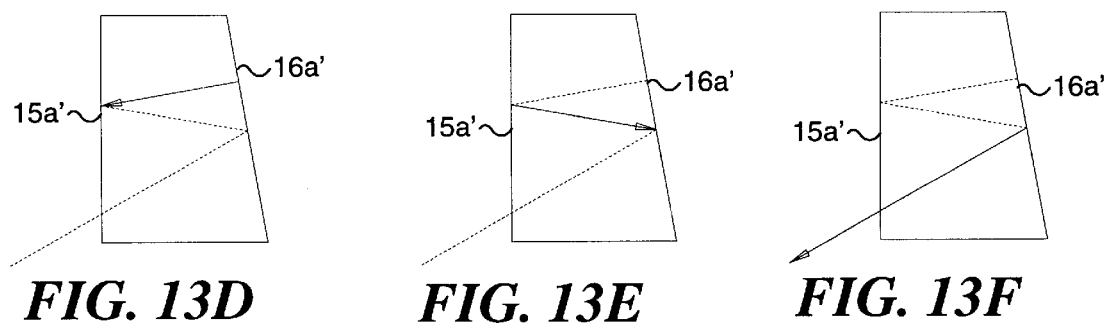
FIG. 13A  FIG. 13B  FIG. 13C
FIG. 13D  FIG. 13E  FIG. 13F

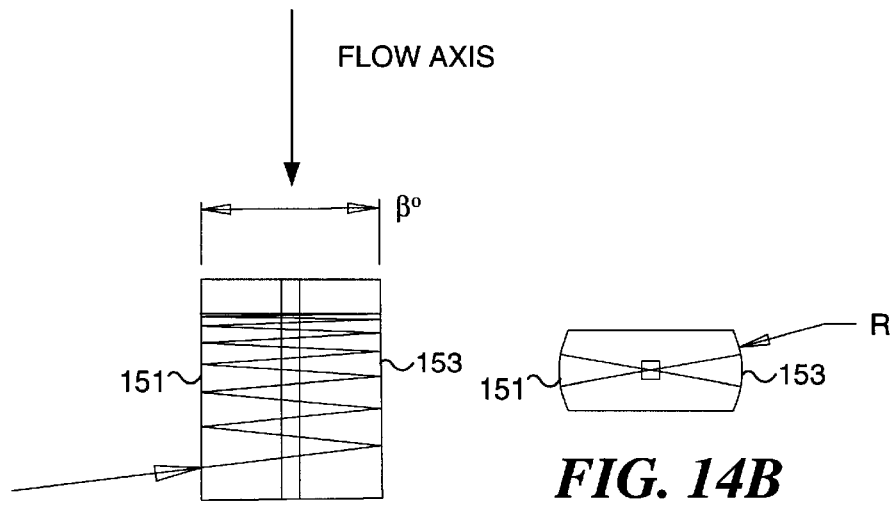
FIG. 14A  FIG. 14B
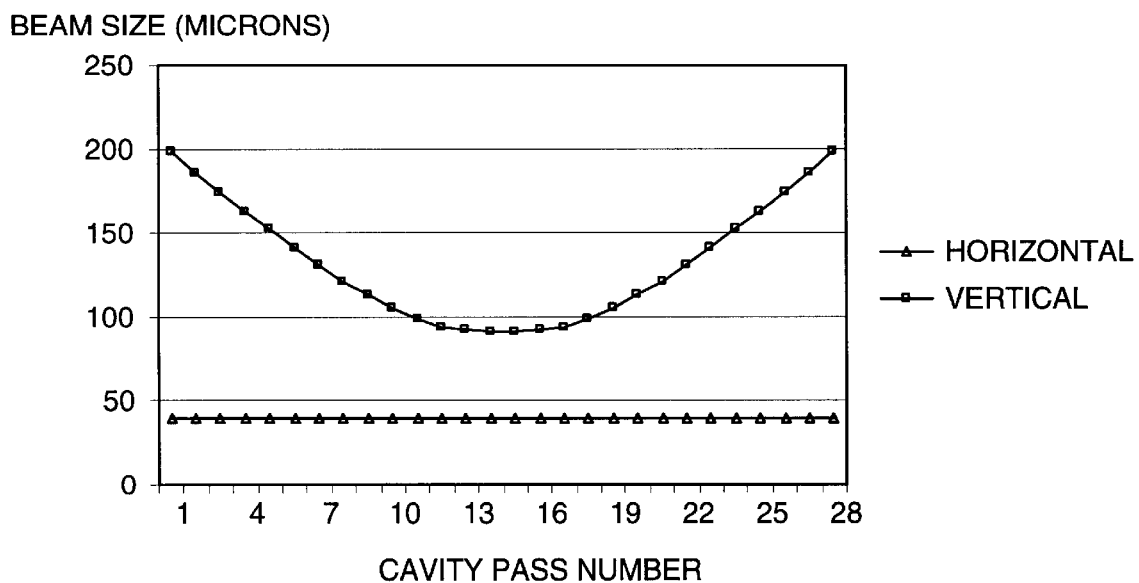
FIG. 15

US 6,580,504 B1

MULTIPASS CAVITY FOR ILLUMINATION AND EXCITATION OF MOVING OBJECTS

RELATED APPLICATIONS

This application is a continuation-in-part of U.S. patent application Ser. No. 09/490,478, filed on Jan. 24, 2000, now U.S. Pat. No. 6,249,341, the benefit of the filing date of which is hereby claimed under 35 U.S.C. §120, which claims the benefit of Provisional application No. 60/117,203, filed Jan. 25, 1999.

FIELD OF THE INVENTION

This invention generally relates to illumination of moving objects or particles for purposes of analysis and detection, and more specifically, to an apparatus and method for increasing the amount of incident light upon these objects to increase scattered, fluorescent, and other signals from moving objects, such as cells, and for detecting the presence and composition of Fluorescence In-Situ Hybridization (FISH) probes within cells.

BACKGROUND OF THE INVENTION

There are a number of biological and medical applications that are currently impractical due to limitations in cell and particle analysis technology. Examples of such biological applications include battlefield monitoring of known airborne toxins, as well as the monitoring of cultured cells to detect the presence of both known and unknown toxins. Medical applications include non-invasive prenatal genetic testing and routine cancer screening via the detection and analysis of rare cells (i.e., cells with low rates of occurrence) in peripheral blood. All of these applications require an analysis system with the following principal characteristics:

1. the ability to carry out high-speed measurements;
2. the ability to process very large samples;
3. high spectral resolution and bandwidth;
4. good spatial resolution;
5. high sensitivity; and
6. low measurement variation.

In prenatal testing, the target cells are fetal cells that cross the placental barrier into the mother's blood stream. In cancer screening, the target cells are sloughed into the blood stream from nascent cancerous tumors. In either case, the target cells may be present in the blood at concentrations of one to five target cells per billion blood cells. This concentration yields only 20 to 100 cells in a typical 20 ml blood sample. In these applications, as well as others, it is imperative that the signal derived in response to the cells be as strong as possible to provide distinct features with which to discriminate the target cells from other artifacts in the sample.

It would be desirable to increase the amount of light incident upon objects in a sample compared to prior art systems, thereby increasing the signal-to-noise ratio (SNR) of a processing system, improving measurement consistency, and thus, increasing the discrimination abilities of the system. A spectral imaging cell analysis system is described in a pending commonly assigned U.S. patent application Ser. No. 09/490,478, filed on Jan. 24, 2000 now U.S. Pat. No. 6,249,341, and entitled, "Imaging And Analyzing Parameters Of Small Moving Objects Such As Cells," the drawings and disclosure of which are hereby specifically incorporated herein by reference. This previously filed application describes one approach that is applicable to imaging. It would also be desirable to obtain many of the benefits disclosed in the above-referenced copending application in non-imaging flow cytometers that employ photomultiplier tube (PMT) detectors and any other system that relies on the illumination of objects within a cavity. Depending upon the configuration, substantial benefits should be obtained by increasing the amount of light incident upon an object by as much as a factor of ten or more. Such an increase in the amount of light would enable the use of low power continuous wave (CW) and pulsed lasers in applications that would otherwise require the use of more expensive high power lasers. However, if high power lasers are used for a light source, a processing system should yield higher measurement consistency, higher system throughput, greater illumination uniformity, and other benefits than has been possible with prior systems.

It is a goal in the design of fluorescence instruments to achieve photon-limited performance. When photon-limited performance is achieved, noise sources in the instrument are reduced to insignificance relative to the inherent statistical variation of photon arrivals at the detector. A good example of photon-limited design is found in non-imaging flow cytometers. The PMT detectors employed in these instruments can amplify individual photons thousands of times with very fast rise times.

Non-imaging cytometers take advantage of the PMT's characteristics to achieve photon-limited performance by making the illuminated area as small as possible. Decreasing the laser spot size reduces the amount of time required for an object to traverse a field of view (FOV) of the detectors. The reduced measurement time, in turn, reduces the integrated system noise, but does not reduce the signal strength of the object. The signal strength remains constant because the reduced signal integration time is balanced by the increased laser intensity in the smaller spot. For example, if the FOV in the axis parallel to flow is decreased by a factor of two, an object's exposure time will decrease by a factor of two, but the intensity at any point in that FOV will double, so the integrated photon exposure will remain constant.

The reduced noise and constant signal strength associated with a reduced FOV increases the SNR of the non-imaging cytometer up to a point. Beyond that point, further reductions in the FOV will fail to improve the SNR because the dominant source of variation in the signal becomes the inherently stochastic nature of the signal. Photonic signals behave according to Poisson statistics, implying that the variance of the signal is equal to the mean number of photons. Once photon-limited performance is achieved in an instrument, the only way to significantly improve performance is to increase the number of photons that reach the detector.

A common figure of merit used in flow cytometry is the coefficient of variation (CV), which equals the standard deviation of the signal over many measurements divided by the mean of the signal. Photon noise, as measured by the CV, increases as the mean number of photons decreases. For example, if the mean number of photons in a measurement period is four, the standard deviation will be two photons and the CV will be 50%. If the mean number of photons drops to one, the standard deviation will be one and the CV will be 100%. Therefore, to improve (i.e., decrease) the CV, the mean number of photons detected during the measurement interval must be increased. One way to increase the number of photons striking the detector is to increase photon collection efficiency. If an increase in photon collection efficiency is not possible, an alternative is to increase the number of photons emitted from the object during the measurement interval. Accordingly, it would be beneficial to provide a system in which illumination light incident on an object but not absorbed or scattered is recycled and redirected to strike the object multiple times, thereby increasing photon emission from the object.

In the case of a conventional imaging flow cytometer, such as that disclosed in U.S. Pat. No. 5,644,388, a frame-based charge-coupled device (CCD) detector is used for signal detection as opposed to a PMT. In this system, the field of view along the axis of flow is approximately ten times greater than that in PMT-based flow cytometers. In order to illuminate the larger field of view, the patent discloses a commonly used method of illumination in flow cytometry, in which the incident light is directed at the stream of particles in a direction orthogonal to the optic axis of the light collection system. The method disclosed in the patent differs slightly from conventional illumination in that a highly elliptical laser spot is used, with the longer axis of the ellipse oriented along the axis of flow. As a result of this configuration, the entire FOV can be illuminated with laser light. Given that a laser is used, the intensity profile across the illuminated region has a Gaussian profile along the axis of flow. Therefore, objects at either end of the field of view will have a lower intensity of illumination light. Unlike a non-imaging flow cytometer, the light collection process disclosed in this patent does not continue for the duration of the full traversal of the FOV. Instead, light is collected from objects at specific regions within the FOV. Object movement during the light collection process is limited to less than one pixel by use of a shutter or pulsed illumination source. As a result, the amount of light collected from an object varies as a function of its position in the field of view, thereby increasing measurement variability. In order to partially mitigate this variation, the illumination spot may be sized so that it substantially overfills the FOV to use an area of the Gaussian distribution near the peak where the intensity variation is minimized. However, this approach has the undesired effect of reducing the overall intensity of illumination, or photon flux, by spreading the same amount of laser energy over a significantly larger area. The end result of reducing photon flux is a reduction in the SNR.

Accordingly, it will be apparent that an improved technique is desired to improve the SNR and measurement consistency of an instrument by increasing photon emission from the object and improving the uniformity of illumination. It is expected that such a technique will also have applications outside of cell analysis systems and can be implemented in different configurations to meet the specific requirements of disparate applications of the technology.

SUMMARY OF THE INVENTION

The present invention is directed to an illumination system that is adapted to increase the amount of signal emitted from an object to increase the SNR and to improve the measurement consistency of devices in which the present invention is applied. In general, there is relative movement between the object and the illumination system, and although it is contemplated that either (or both) may be in motion, the object will preferably move while the illumination system is fixed. In addition, it should also be understood that while this discussion and the claims that follow recite "an object," it is clearly contemplated that the present invention is preferably intended to be used with a plurality of objects and is particularly useful in connection with illuminating a stream of objects.

The present invention increases the amount of light incident upon an object as the object traverses a field of view, without incurring the expense of additional or more powerful light sources. It also may be configured to increase the uniformity of illumination in the field of view.

In a first embodiment of the present invention, a reflection cavity is formed by the placement of two mirrors on either side of a moving stream of objects. A light collection system is disposed substantially orthogonal to a plane extending through the mirrors and the stream. The light collection system is configured to collect light over a predefined angle and within a predefined region or field of view between the mirrors. Accordingly, the light collection system collects light that is scattered or emitted from objects as they traverse the space between the mirrors. The scattered or emitted light that is collected is directed onto a detector.

A light from a light source is directed through the stream of moving objects in a direction nearly orthogonal to the stream of objects but slightly inclined in the plane that extends through the mirrors and the stream. With cells and most other objects, only a small fraction of the incident light interacts with the objects via absorbance or scatter. The rest of the light passes through the stream, and is then redirected by reflection from a surface back into the stream of moving objects. The light leaves the reflecting surface at a reflected angle that is equal to an incident angle of the light. Due to the reflection angle and the distance between the stream and the first surface, the light intersects the stream on the second pass at a position that is displaced from that at which the light passed though the stream on its initial pass. The light continues through the stream and is redirected by a second surface on the other side of the stream, which is substantially parallel to the first surface, back towards the stream. Again, as a result of the reflection angle and the distance between the second surface and the stream, the light passes through the stream on the third pass at a position that is displaced from that of the second pass. The reflection of the light through the stream continues a plurality of times until the light has traversed a distance along the direction in which the stream is flowing that is substantially equal to the collected field of view of the light collection system. At this point, the light is no longer reflected back through the stream, but is preferably caused to exit the illumination system.

It should be understood that most of the light that passes through the stream is largely unimpeded by the stream or objects in the stream. Therefore, upon subsequent passes, substantial light remains to intercept the object or objects in the stream. By "recycling" light in this manner, the light that would normally be wasted is employed to illuminate the object each time the object passes through the light. Consequently, the SNR of the instrument is substantially improved by increasing the amount of scattered and/or emitted light that is incident on the detector.

The present invention can also be configured so as to obtain a desired illumination profile along the axis of flow. The beam size and traversal distance can be adjusted to create a predefined amount of overlap between beams at the stream intersection point to homogenize the intensity profile along the axis of flow. Further, the input beam can be apertured to use a section of the beam with less variation to further increase illumination uniformity along the flow axis.

In a second embodiment of the invention, the beam is reflected back upon itself after numerous traversals of the cavity. In this embodiment, the total number of traversals is doubled relative to the first embodiment, thereby increasing the number of photons incident upon the stream.

In a third embodiment, a slight angle is introduced between the mirrors which causes the angle of incidence to gradually decrease as the beam traverses the cavity. Eventually the traversal direction reverses, causing the beam to traverse the cavity in the opposite direction, thereby increasing the number of times the beam traverses the stream.

In a fourth embodiment, the present invention can be configured such that the surfaces which redirect the beam back into the stream contain optical power in one or both axes in order to create one or more traversal reversals of the beam a to optimally size the beam at or near the intersection points with the stream.

BRIEF DESCRIPTION OF THE DRAWING FIGURES

The foregoing aspects and many of the attendant advantages of this invention will become more readily appreciated as the same becomes better understood by reference to the following detailed description, when taken in conjunction with the accompanying drawings, wherein:

FIG. 12 is an isometric view of an embodiment of the present invention that employs a retro-reflector to reverse beam traversal, increasing the number of times the beam traverses the flow stream;

Figure 16:
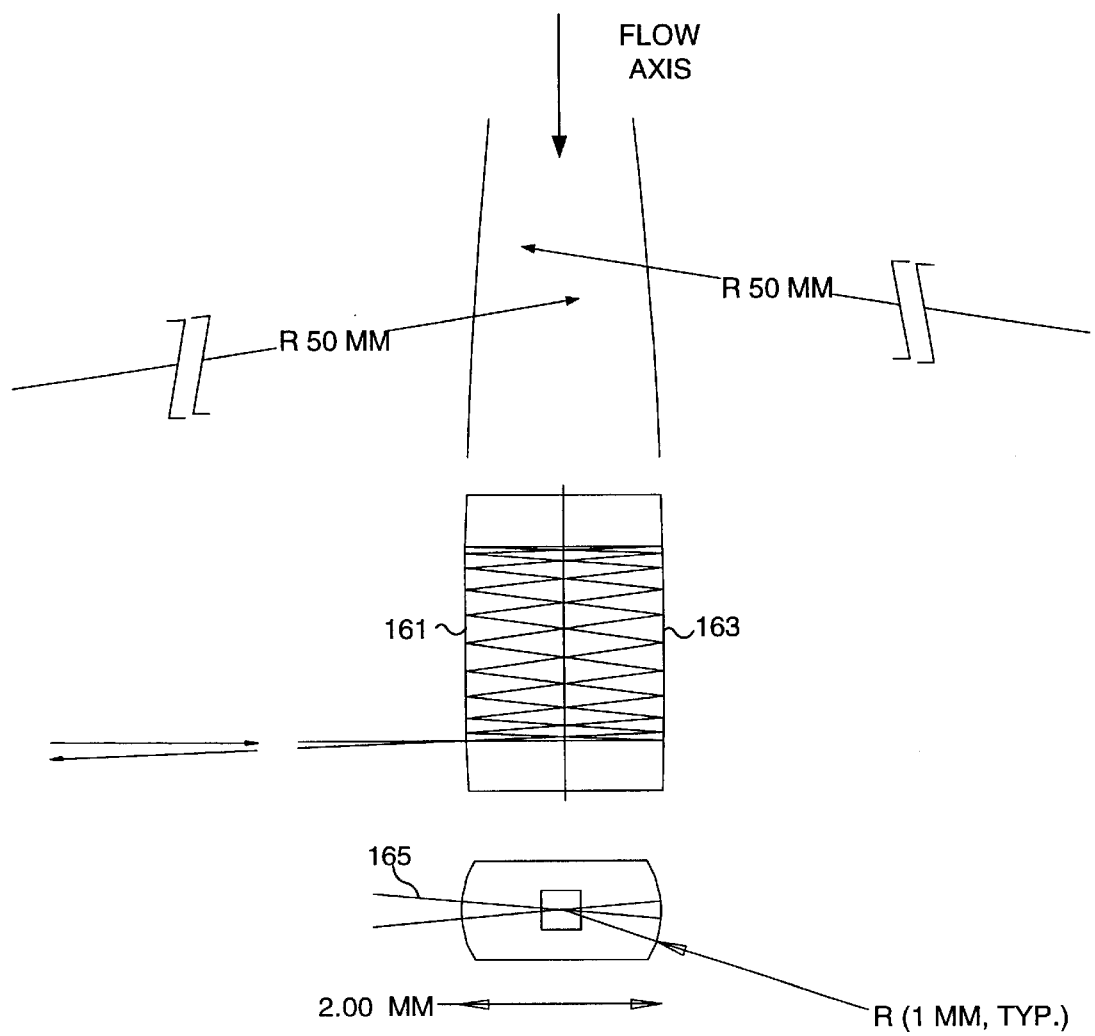
Figure 17:
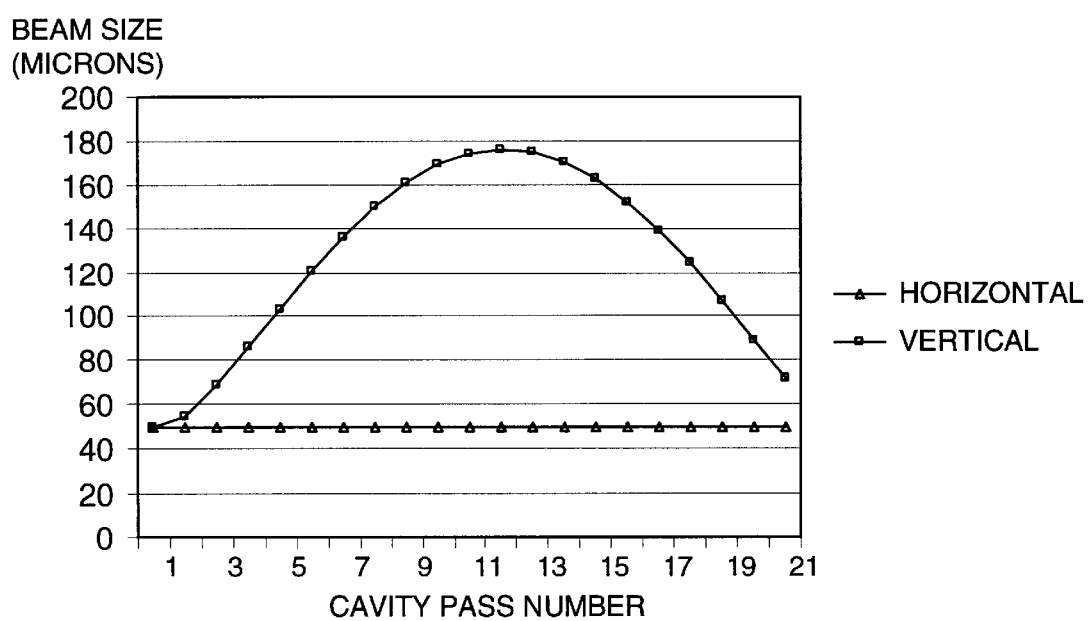

FIGS. 13A–13F schematically illustrate an embodiment of the present invention where the beam traversal direction is reversed after a plurality of passes across the cavity by introducing an angle between the cavity mirrors;

FIGS. 14A–14B further illustrate schematically an embodiment of the present invention wherein the beam traversal direction is reversed after a plurality of passes across the cavity by introducing an angle between the cavity mirrors and in which the mirrors provide an optical power about an axis parallel to the flow axis for refocusing the beam in the horizontal axis with each pass through the cavity;

FIG. 15 is a plot of the beam size in the horizontal and vertical axes for each pass of the beam across the cavity in an embodiment employing 28 passes, as illustrated in FIGS. 14A–14B;

FIG. 16 schematically illustrates an embodiment of the present invention wherein the cavity mirrors have a toroidal surface profile and provide an optical power in both the horizontal and vertical axes for inducing a reversal of beam traversal direction and for refocusing the beam in both axes; and FIG. 17 is a plot of the beam size in the horizontal and vertical axes for each pass of the beam across the cavity in an embodiment employing 21 passes of the beam where the walls of the cavity have the toroidal surface profile illustrated in FIG. 16.

DESCRIPTION OF THE PREFERRED EMBODIMENT

The present invention offers considerable advantages over the prior art for illumination of cells and other types of particles in a flow stream. These advantages arise from the recycling of laser light to increase the photon flux incident upon objects in a flow stream. The present invention can also be configured to improve the uniformity of illumination, while at the same time increasing the photon flux incident upon objects, which is expected to enhance the performance of various flow cytometry applications.

Figures 1, 2:
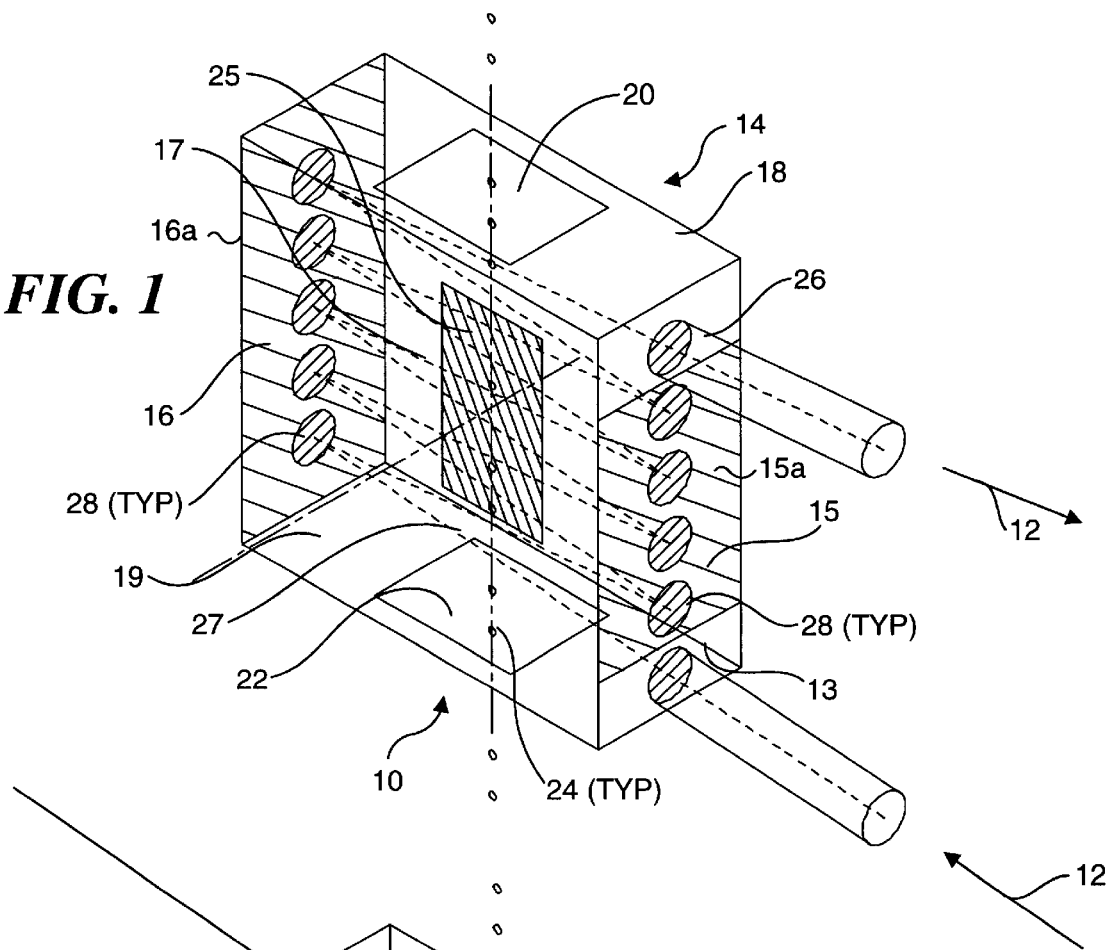
FIG. 1 is an isometric view of an illumination system corresponding to a first embodiment of the present invention.
FIG. 2 (Prior Art) is an isometric view of a conventional method for illuminating objects in a flow stream.

A first preferred embodiment of an illumination system 10 in accord with the present invention is shown in FIG. 1. Illumination system 10 includes a rectangular solid glass substrate 14 with reflective coatings 15 and 16 applied to two substantially parallel and flat outer surfaces 15a and 16a of the glass substrate. A channel 20 is disposed in the rectangular solid to enable a plurality of objects 24 in a flow stream to pass through illumination system 10 between surfaces 15a and 16a. As is commonly done, the objects may be entrained in a sheath flow (not shown) in order to keep them centered within channel 20. A substantially cylindrical beam of light 12, such as that emitted by a laser source (not shown), is directed toward an uncoated area 13 in surface 15a of the substrate such that a propagation axis of the beam of light (indicated by the arrow) is at a slight angle with respect to a normal to surface 15a. The beam proceeds through surface 15a and passes through at least a portion of the plurality of objects 24 and is then reflected from reflective coating 16 back into the plurality of objects 24. The angle of propagation axis 12a is set such that as beam of light 12 traverses the substrate, it rises a predefined amount, intersecting surface 15a in reflective coating 15 above uncoated area 13. The beam reflects from reflective coating 15 and again passes through the plurality of objects 24.

As objects 24 flow along the channel, corresponding images of the objects are produced with an optical system (not shown in this Figure) having a field of view 25. As shown in FIG. 1, light beam 12 continues to traverse substrate 14 such that it passes through the substrate ten times, thereby illuminating all of field of view 25, before it is allowed to pass out of the substrate through an uncoated area 26 in surface 15a. Reflection spots 28 and dashed lines 27 illustrate the path of the light beam and indicate the points where the beam intersects and reflects from reflective coatings 15 and 16. Reflective coatings 15 and 16 form a reflection cavity 17 through which the plurality of objects 24 pass. Those skilled in the art will appreciate that surfaces 15 and 16 could be independently mounted on their own substrates without the use of the glass substrate 14. By reflecting the light back and forth in this manner, the total amount of light incident on objects 24 is substantially increased over that provided by conventional illumination methods.

In contrast to the foregoing configuration, FIG. 2 illustrates a common approach used in the prior art to illuminate objects in flow cytometers such as those described in U.S. Pat. No. 5,644,388. In this configuration, an elliptical-shaped beam of light 30 is directed through the substrate 36 and passes through the plurality of objects 24. In order to illuminate all of field of view 38, the light beam size in the flow axis is made substantially larger than that used in the present invention. As a result, the intensity of light at any point in field of view 38 is substantially less than in the present invention, which reduces the amount of light scattered or otherwise emitted from the plurality of objects 24, thereby reducing the SNR of the conventional approaches relative to the SNR of the present invention. Likewise, in the conventional approach, the illumination intensity varies across the field of view in accordance with a Gaussian intensity distribution of the illuminating laser light.

Figure 3:
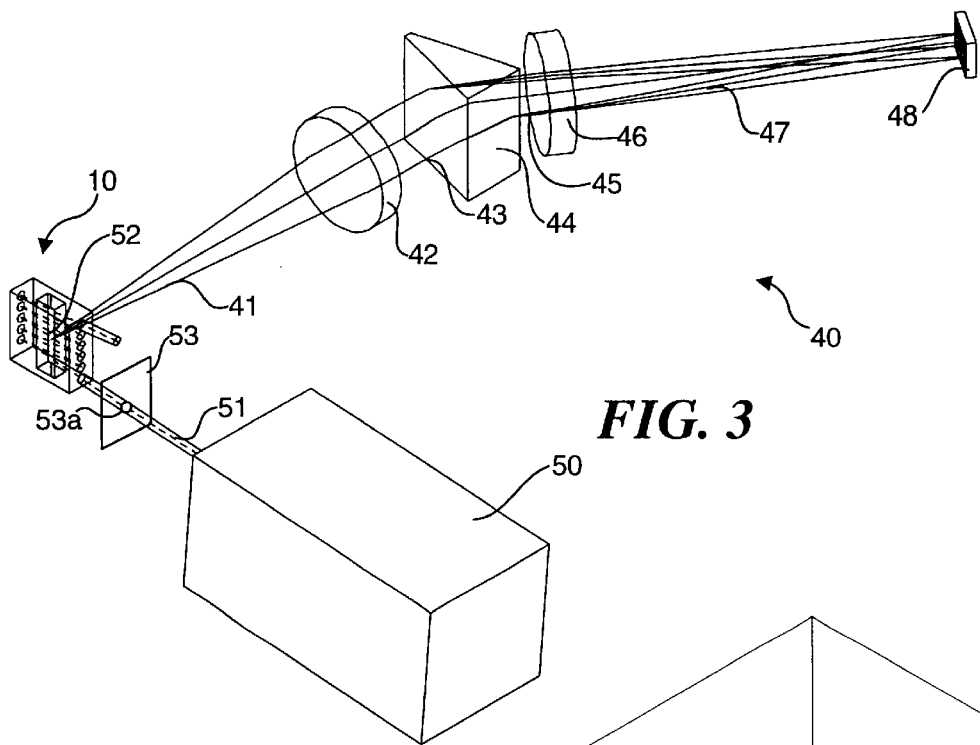
FIG. 3 is an isometric view of an exemplary imaging system that implements the illumination system of FIG. 1.

FIG. 3 shows an exemplary imaging system 40 that is substantially similar to imaging systems disclosed in copending commonly assigned U.S. patent application Ser. No. 09/490,478, the specification and drawings of which have been specifically incorporated herein by reference. The present invention is employed for illumination in imaging system 40. In this imaging system, light 41 from an object passes through a collection lens 42, which collects the light, producing collected light 43. The collected light is focussed substantially at infinity, i.e., the rays of collected light 43 are generally parallel and enter a prism 44, which disperses the light, producing dispersed light 45. The dispersed light enters an imaging lens 46, which focusses light 47 on a time-delay-integration (TDI) detector 48.

Imaging system 40 includes illumination system 10, which was discussed above. A laser light source 50 directs a beam of coherent light 51 toward a reflection cavity 52 within illumination system 10, as shown in the Figure. Optionally, the illumination system may further include an aperture plate 53, which includes an aperture 53a having a diameter selected to reduce the size of the beam sufficiently so that the light intensity distribution across the cross section of the beam that has passed through the aperture is substantially constant. It should be noted that the present invention may be included in other imaging systems that are described and illustrated in the above referenced copending patent application.

Figure 4:
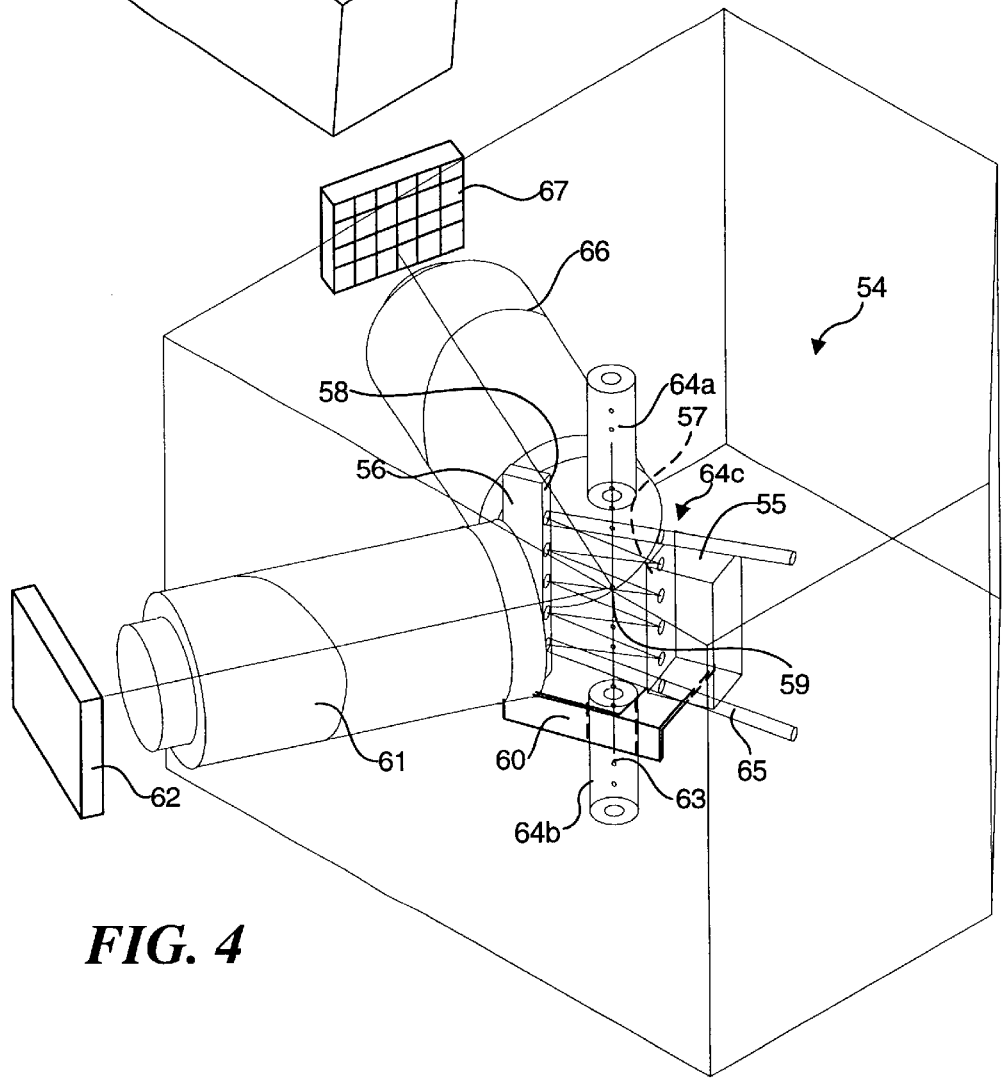
FIG. 4 is an isometric view of an embodiment of the present invention using mirrors immersed in a fluid.

The present invention can also be configured for implementation in a stereoscopic imaging flow cytometer. This configuration of the present invention is shown in FIG. 4 where a reflection cavity 59 is created by supporting two mirrors 55 and 56 on independent substrates within an immersion medium of an imaging flow cytometer. The ends of two capillary tubes 64a and 64b are brought within close proximity to each other. A stream of objects 63 is hydrodynamically focused with capillary tube 64a and caused to flow through a gap 64c between the tubes and into capillary tube 64b. Two water immersion objectives 61 and 66 are mounted on a frame (not shown) and are employed to image the gap between the capillary tubes onto two pixilated detectors 62 and 67. Mirrors 55 and 56, which are supported within the immersion cavity on a frame 60, create reflection cavity 59 around the stream of objects 63. Light from an illumination source (not shown) is directed along a path 65 under mirror 55, through stream of objects 63, and onto mirror 56. Upon striking the mirror, the light is redirected back through stream of objects 63, and caused to again traverse the stream of objects, generally in the manner described above, in regard to FIG. 1.

The foregoing Figures illustrate several of the various optical system configurations that include the present invention. Those skilled in the art will appreciate the present invention may be used to advantage in imaging as well as non-imaging flow cytometers. The following discussion numerically quantifies the advantage of using an embodiment of the present invention in a non-imaging PMT-based flow cytometer. The signal strengths are compared for three different illumination systems, two of which are in the prior art, and one of which is an embodiment of the present invention.

Figure 5:
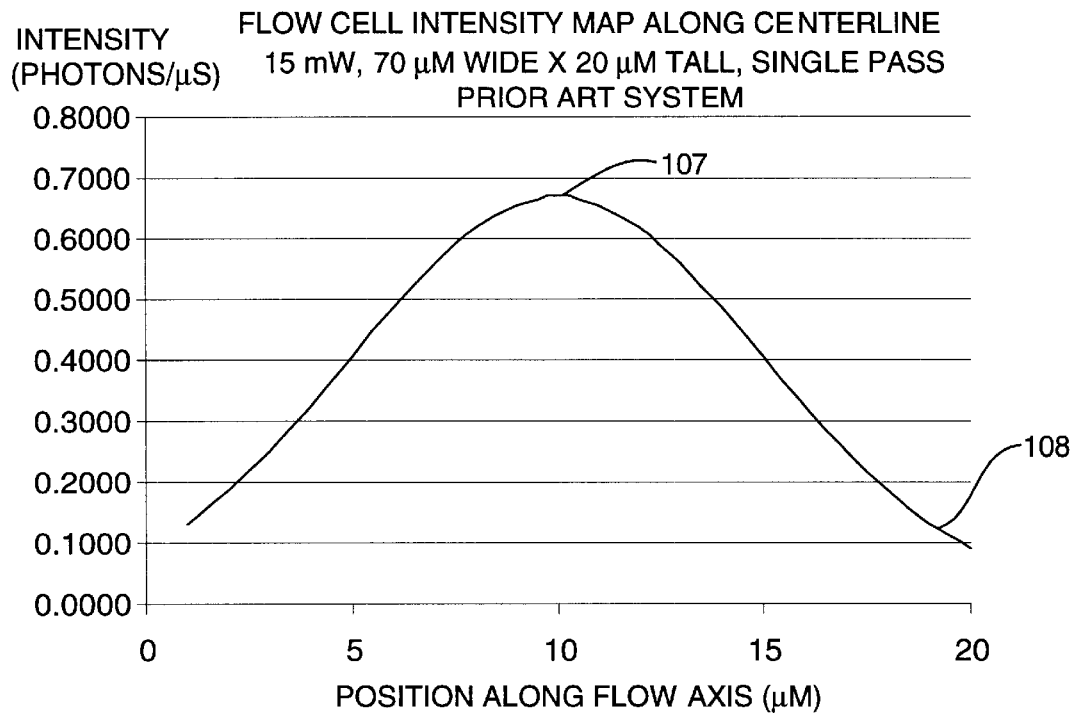
FIG. 5 is an XY plot showing an illumination intensity profile for a conventional (Prior Art) single pass illumination scheme with a short FOV.

The first prior art system to be discussed is incorporated in a widely-available, non-imaging commercial flow cytometer system. This system employs a 15 mW continuous wave laser that produces an elliptical beam spot 70 microns wide by 20 microns tall, a 6 m/s sample flow rate, and a PMT detector (not shown). An intensity profile along a flow path of the illumination system is illustrated in FIG. 5. The profile has a peak intensity 107 that is approximately 0.68 photons/ microsecond through the area defined by the absorbance cross section of a fluorescein molecule. The intensity varies over the field of view of the collection system in accordance with a Gaussian distribution function, $1/e^{2x}$, wherein "x" is a ratio of the distance along the traversal path to the radius of the beam. Conventionally, the boundaries of a Gaussian beam are defined at a $1/e^2$ point 108, which is the position at which the intensity falls to approximately 13% of the peak intensity. For this illumination profile, each fluorescein molecule emits an average of 1.29 photons as it traverses the illuminated region. Those skilled in the art will appreciate that the emission of photons is quantized (no fractional photons are emitted) and that some molecules emit no photons, while others emit one or more photons when traversing the illuminated region. However, the resulting average number of emissions per molecule over all molecules is a fractional number.

Figure 6:
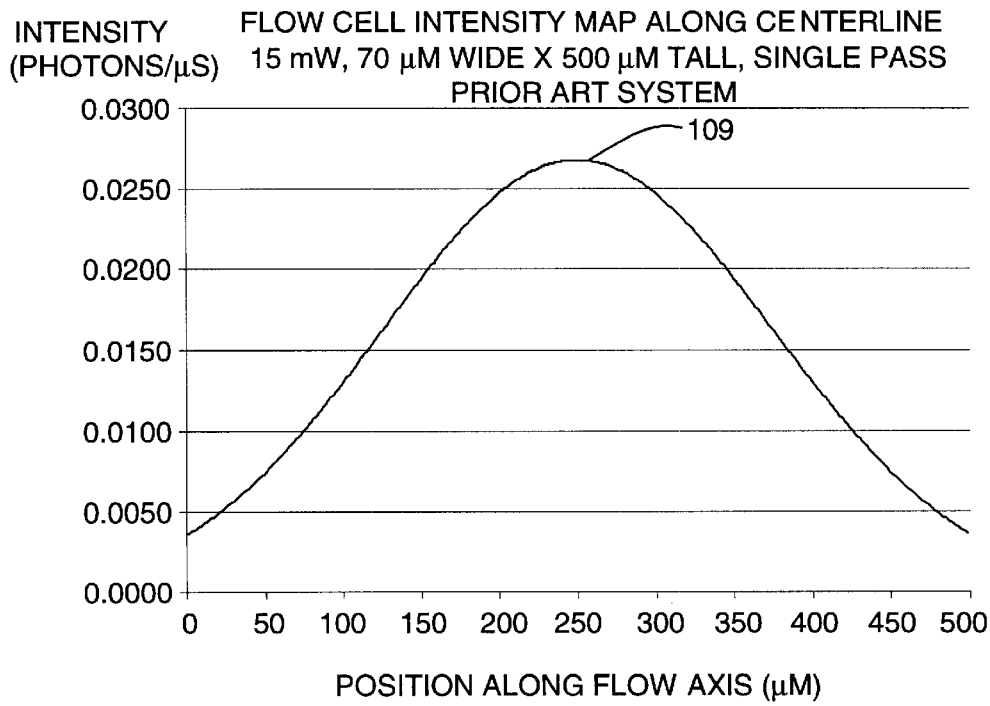
FIG. 6 is an XY plot showing an illumination intensity profile for a conventional (Prior Art) single pass illumination scheme with a tall FOV.

The second prior art example is the same as the first except that the dimension of the illuminating beam is 500 microns in the axis parallel to the direction of object flow. FIG. 6 illustrates an intensity profile for the enlarged illumination area produced by this second prior art system. A peak intensity 109 for this profile is approximately 0.027 photons/microsecond, which is 25 times lower than in the first example shown in FIG. 5. Despite the lower peak intensity, the average emission per fluorescein molecule remains 1.29 photons due to the increased illumination time allowed by the taller beam. Because there is no difference in the average emission per fluorescein dye molecule in the two prior art systems, there is no change in instrument performance, despite the 25-fold change in beam height. Changes in the beam height along the axis of the flow stream do not change the number of fluorescent photons emitted by the sample as it flows through the illuminated region, because the increased illumination time is offset by a corresponding reduced photon flux per unit area.

Figure 7:
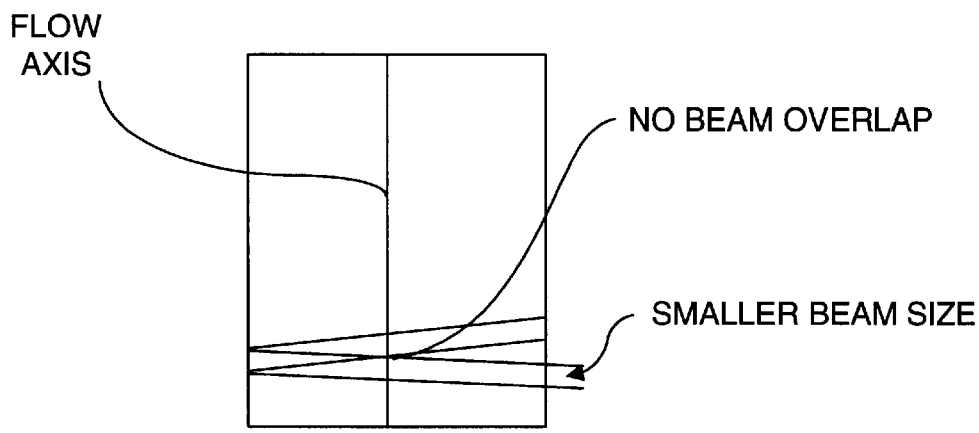
FIG. 7 is a schematic diagram illustrating a condition in which no beam overlap occurs at the center of the cavity when a smaller beam size is used in a preferred embodiment of the present invention.

FIG. 7 illustrates an embodiment of the present invention wherein the beam height is 100 microns in the axis parallel to flow, and the beam is reflected across the illuminated region five times. The beam incident angle is inclined relative to the reflecting surfaces so that there is no overlap of the beam in the center of the cavity. The resulting total illuminated height is therefore 500 microns, like that of the second prior art example discussed just above. In this embodiment of the present invention, the beam width is increased from the 70 micron dimension in the prior art, to 90 microns in order to reduce beam divergence. With the configuration used in this embodiment of the present invention, the average number of photons emitted per dye molecule is increased to 4.78 photons, more than a factor of three greater than is obtained using conventional illumination in the prior art. The increase in emitted photons is a result of two factors: (1) high illumination flux due to compact beam dimensions; and (2) an extended illumination height (and correspondingly longer illumination time), due to the multiple offset passes of the laser beam through the illumination region.

Figure 8:
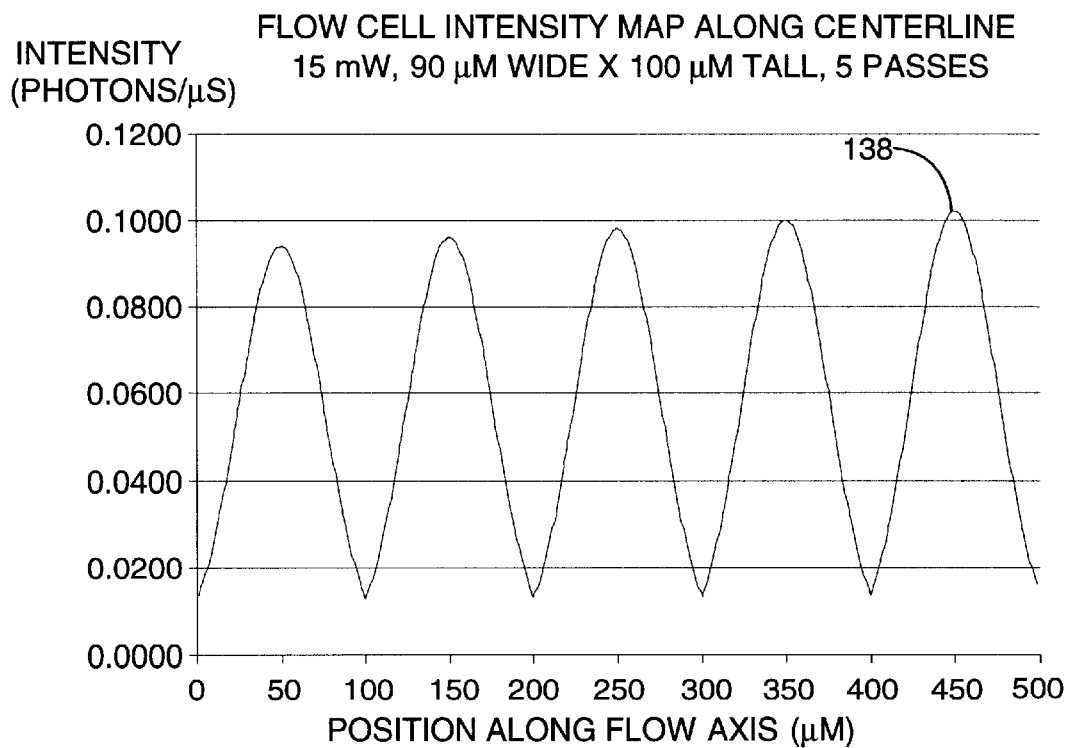
FIG. 8 is an XY plot showing an illumination intensity profile for the embodiment of the present invention illustrated in FIG. 7, but for the case in which a narrow light beam passes through a field of view five times.

The intensity profile along the stream axis, which provides the increased illumination flux of the above embodiment, is illustrated in FIG. 8. From FIG. 8, it is apparent that a five-pass embodiment produces a peak intensity 138 of more than 0.10 photons/microsecond through the area defined by the absorbance cross section of the fluorescein molecule, which is four times greater than that shown in FIG. 6 for the prior art illumination configuration with the same illumination height. The increase in intensity of the exciting beam and the increase in the number of passes in which the exciting beam encounters a molecule in the present invention produce more fluorescence from each molecule of the dye.

Figure 9:
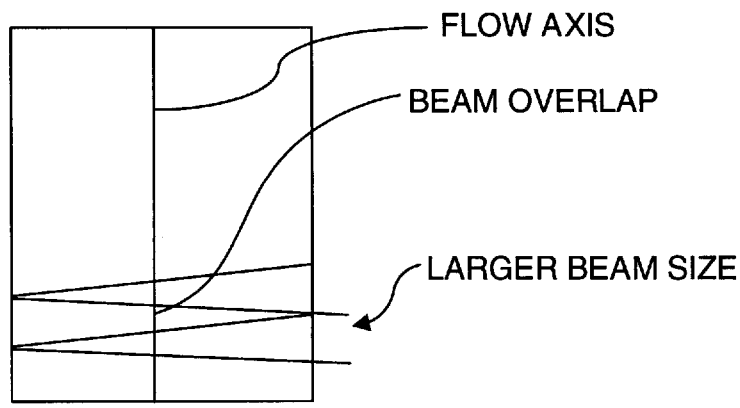
FIG. 9 is a schematic diagram illustrating a condition in which significant beam overlap occurs at the center of the cavity when a larger beam size is used in a preferred embodiment of the present invention.
Figure 10:
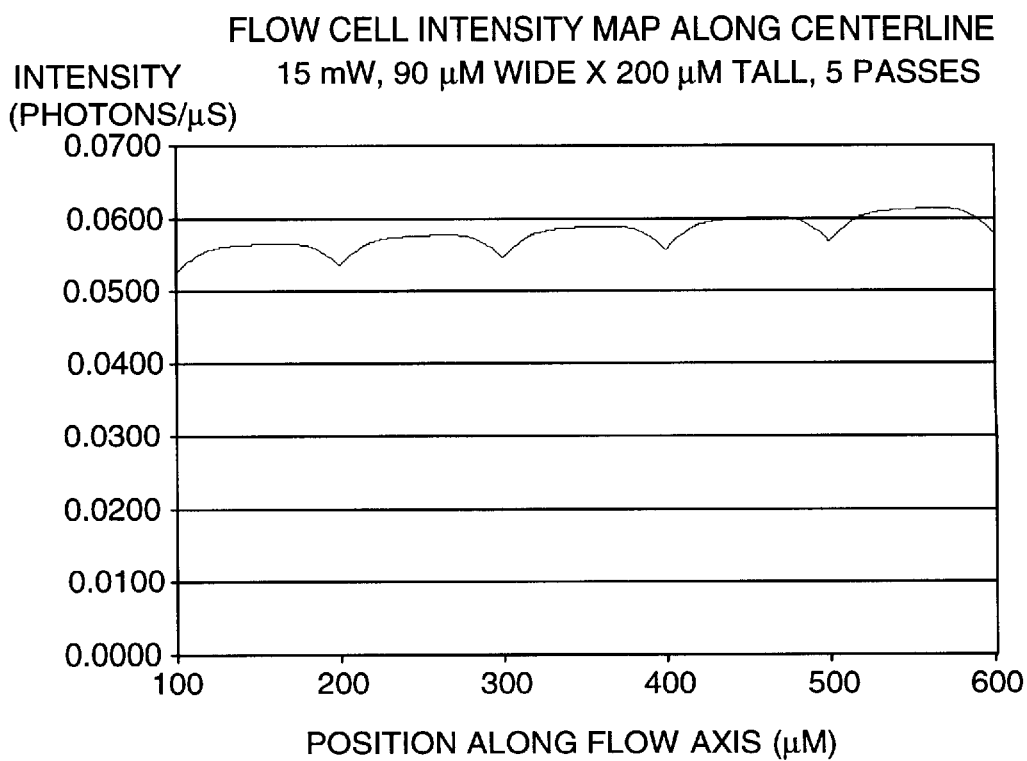
FIG. 10 is an XY plot showing an illumination intensity profile for the embodiment of the present invention illustrated in FIG. 9, but for the case in which a wide light beam passes through a field of view five times.

In addition to increasing illumination intensity, the present invention enables control of the illumination intensity profile in the cavity at the intersection of the stream and each of the plurality of beam passes. By appropriately choosing a waist size and the incident angles, an advantageous illumination profile may be achieved. For applications of the present invention in imaging flow cytometers, it may be advantageous to create a more uniform illumination intensity profile in the cavity, to decrease measurement variation. FIG. 9 shows a configuration similar to that of FIG. 7, except that the beam height is increased to produce a 50% overlap between beam segments in adjacent passes. FIG. 10 shows the resulting intensity profile, which is of much higher uniformity than is produced under no-overlap conditions. In addition to changing the beam size, the extent of beam overlap from pass to pass can be controlled by modifying the distance between the cavity's reflective surfaces and by changing the incident angle of the beam. Increasing the distance between the reflective surfaces and/or the incident angle enables the beam to propagate farther along the vertical axis between passes across the center of the cavity.

Figure 11:
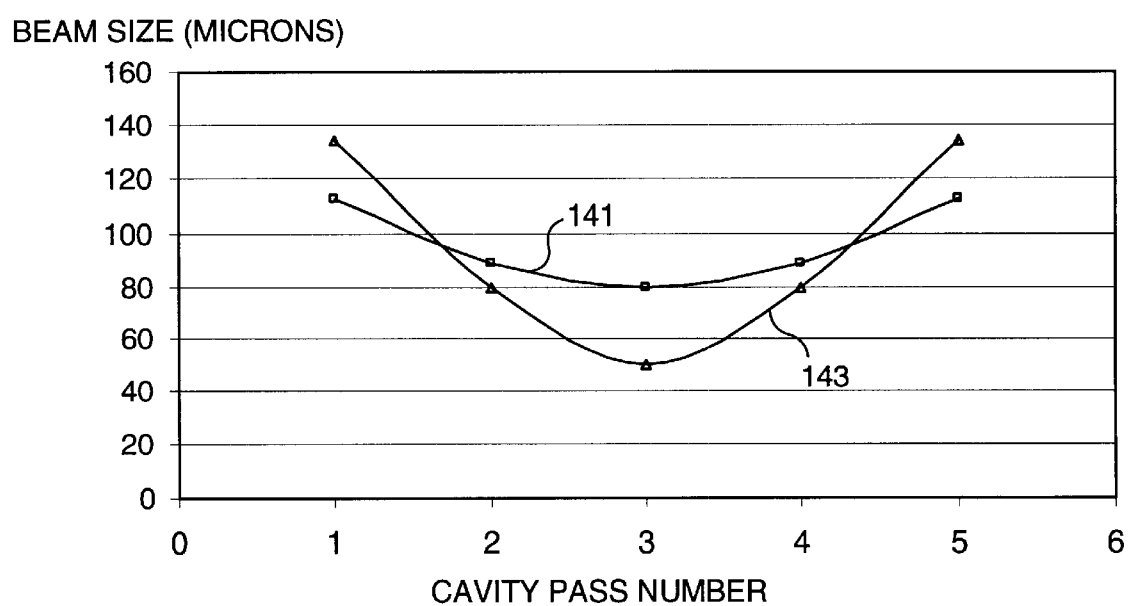
FIG. 11 is a plot of the beam size in the horizontal axis for two beams with different waist sizes in a five pass embodiment of the invention, illustrating how a larger waist size can produce a smaller average beam size, thereby increasing the overall intensity of light incident on the stream.

In addition to the factors that cause beam overlap noted above, beam overlap can occur as a result of a divergence of the beam as it traverses the cavity. Divergence due to diffraction causes the cross-sectional area of the beam to increase as the beam traverses the cavity. As the traversal distance increases, a concomitant increase in cross-sectional beam area, or beam spread occurs. This increase in beam spread decreases the intensity, or photon flux at any given portion in the cross section of the beam, which in turn, reduces the probability of fluorescence excitation of probe molecules. Therefore, the beam spread must be kept within acceptable limits. In accord with the embodiments of the present invention discussed above, the beam waist, i.e., the point of the smallest cross-sectional area of the beam, is preferably at a midpoint of the beam traversal through the cavity. The beam cross-sectional size increases in either direction away from the waist at a rate that is inversely proportional to the size of the waist. This phenomenon is illustrated in FIG. 11, which shows the spread of two beams over five passes across the center of a 5 mm wide cavity, one beam having a 50 micron waist (line 141 with triangles at data points) and the other an 80 micron waist (line 143 with squares at data points). Even though a 50 micron waist is substantially smaller in diameter than an 80 micron waist, the average beam diameter throughout the entire traversal of the 50 micron beam is larger. Those skilled in the art will appreciate that in view of the beam divergence, the waist size may be chosen appropriately to maximize intensity based on the number of cavity traversals and the acceptable beam size at points away from the waist, or in regard to the average beam size within the cavity. Those skilled in the art will also appreciate that the beam waist may be disposed appropriately within or outside the cavity to achieve a desired effect with the present invention.

Within the scope of the present invention, various parameters can be adjusted to increase the number of cavity traversals the beam makes while maintaining a beam size that is appropriate to increase fluorescence. For example, the cavity may be made narrower to decrease the path length that the beam must travel as it traverses the cavity. In this manner, the number of passes in the cavity can be increased while still maintaining a small cross-sectional beam size and thereby maintaining relatively high beam intensity.

FIG. 12 shows an embodiment of an illumination system 10' in accord with the present invention in which a retro-reflector 139 is included to reflect the beam back into the cavity after it has exited the top of the cavity. In all other respects, the embodiment shown in this Figure is substantially identical to the first preferred embodiment shown in FIG. 1. However, in the embodiment of FIG. 12, retro-reflector 139 reflects the beam back along the path it followed before exiting the cavity, so that the beam reversing its previous path through the substrate. This embodiment effectively doubles the number of beam passes through the cavity achieved by the embodiment in FIG. 1. A 20-pass retro-reflected embodiment will provide nearly a 15-fold increase in the average photon exposure of an object over a conventional single-pass illumination.

FIGS. 13A–13F illustrate another embodiment of the present invention wherein the beam traverses the cavity and reverses direction, but unlike the embodiment of FIG. 12, it does so without the use of a retro-reflector. In this embodiment, an angle is introduced between two surfaces 15a' and 16a', which comprise the walls of the cavity. For illustration purposes, the angle between the reflecting surfaces is exaggerated and shown as equal to ten degrees. As will be observed in the Figure, the introduction of the angle between the two surfaces causes a gradual reduction in the incident angle of the beam relative to the surfaces, as the beam repeatedly traverses the cavity. Eventually, the incident angle becomes 90 degrees, or reverses sign, and the beam is reflected back upon itself (or down the walls of the cavity) and re-traverses the cavity in the opposite direction.

As illustrated earlier in FIG. 11, the cross-sectional beam size converges to a minimum at the waist position then diverges. The intensity of the beam at any point is inversely proportional to the square of the beam diameter. In order to maintain a high beam intensity, it is therefore advantageous to maintain a small beam diameter as the beam traverses the cavity. To achieve this goal, the embodiment of the present invention shown in FIGS. 14A and 14B incorporates optical power in the reflecting surfaces of the cavity. Each wall of the cavity is a cylindrical mirror 151 and 153 with curvature in the horizontal plane selected to focus the light beam that is reflected therefrom within the cavity. The center of each wall's radius of curvature, R, is the flow stream, so with each reflection of the light beam, the diverging beam is refocused by the mirrors on the objects within the flow stream. As a result, a small beam diameter is maintained in the vicinity of the flow stream, and the beam spread in the axis perpendicular to flow is minimized so that more light is focused on the objects in the stream than could otherwise be obtained. The embodiment shown in FIGS. 14A and 14B also incorporates the method of beam reversal illustrated in FIG. 13. The size of a 488 nm laser beam waist in the vertical and horizontal axes for this embodiment is plotted in FIG. 15. The beam size in the axis perpendicular to flow is maintained at 40 microns in the vicinity of the flow stream. As the beam propagates up the cavity, the beam diameter alternately converges on the flow stream and then diverges toward the reflecting surface where, upon reflection, the beam re-converges near the flow stream. In this embodiment of the present invention, the cylindrical surface contains no optical power in the axis of flow. Therefore, the beam diameter upon the first intersection with the stream is 199 microns. The beam continues to converge up to the 14$^{th}$ pass where the beam waist, or minimum beam diameter, of 91 microns is reached. The use of the tilted surface wall or the use of a retro-reflector where the beam exits enables the beam to traverse back down the cavity, providing a total of 28 passes of the beam through the flow stream. A flow cytometer employing this embodiment, with a 28-pass cavity, produces an average photon emission per dye molecule of 44.32 photons. This result represents a 35-fold increase in signal strength compared to the conventional method of illumination, where only a 1.29 photon per molecule average emission is achieved.

As a further embodiment of the present invention, optical power can be provided in both the vertical and horizontal axes of the cavity walls. FIG. 16 illustrates an alternative embodiment of the present invention where the reflection cavity surfaces 161 and 163 are toroids with a radius of 50 mm about an axis perpendicular to the page and a radius of approximately 1 mm about the axis along the flow stream. The centers of curvature for the 50 mm surfaces are separated by approximately 98 mm, so that the vertex of each mirror is separated by 2 mm and centered on the flow stream axis. The illumination beam enters the reflective cavity perpendicular to the flow stream axis at a point approximately 1 mm below the axis defined by a line running between the centers of curvature for the two 50 mm surfaces. Along the axis of beam propagation, the beam waist is located within the reflective cavity and the beam makes a first flow stream intersection. The beam traverses the cavity and is reflected upward at an angle of approximately 2.3 degrees from horizontal, causing the beam to re-cross the cavity and strike the other wall of the cavity. The beam reflects from this cavity wall at an angle of about 4.4 degrees with respect to horizontal and continues to re-cross the cavity and strike the opposite surface in this manner such that the reflected angle with the horizontal increases upon each reflection of the beam by one of the surfaces. After the sixth reflection, the beam traverses the cavity and crosses the axis defined by a line 165 running between the centers of curvature of the two 50 mm radii surfaces 161 and 163. At this point, the normals to these surfaces point downward. Therefore, the reflected angle of the beam with respect to the horizontal decreases. At the first reflection after the beam crosses the axis defined by the centers of curvature of the surfaces, the reflection angle of the beam with respect to the horizontal is approximately 8.1 degrees. At the second reflection after crossing the axis, the reflection angle is reduced to approximately 7.4 degrees. At the eleventh reflection, the beam makes an angle of approximately zero degrees to the horizontal, and after striking the other wall, the propagation direction of the beam with respect to the flow axis is reversed. The beam then propagates down the cavity, reflecting from the surfaces and eventually exits the cavity at its point of entry after making twenty two passes through the flow stream.

FIG. 17 illustrates the beam waist size during the propagation of a 488 nm laser beam through the embodiment of the invention illustrated in FIG. 16, where the reflecting surfaces have optical power in both axes. The beam intersects the flow stream on the first pass with a 50 micron waist in each axis. After the beam passes through the stream it begins to diverge and strikes the far wall of the cavity. Upon reflection, the beam re-converges in the vertical plane such that the waist is approximately 50 microns when it crosses the flow stream. As described in the previous embodiment the beam always re-converges at the flow stream with a waist size of 50 microns in the vertical plane after striking the cavity wall. However, in the axis parallel to flow the beam continues to diverge after reflecting off the cavity wall. The optical power in that axis is insufficient to cause the beam to re-converge. Therefore, when the beam intersects the flow axis on the second pass, it is approximately 55 microns in the axis parallel to flow. The optical power in the axis parallel to flow reduces the divergence from what it would be if the surface contained no optical power in the that axis, but the divergence continues to increase as the beam enters the far field propagation regime. Ultimately, after reflecting from the left hand and right hand surfaces of the cavity eleven times, the beam begins to re-converge in the axis parallel to flow. At this point the beam waist is approximately 176 microns. From this point on the beam begins to converge back toward a 50 micron waist, but exits the cavity before reaching a dimension of 50 microns in the axis parallel to flow.

Those skilled in the art will appreciate that in all the cases described thus far, the F-number of each of the optical systems described is in excess of 40 and therefore, from an aberration perspective, the optical performance is very well behaved, and the spot sizes of the beam in each axis are dictated by diffraction theory. Therefore, constant radius surfaces may employed. However, those skilled in the art will also appreciate that for lower F-numbers, or smaller spot sizes, aspheric or non-constant radii surfaces may be employed to control wave front aberrations.

Although the present invention has been described in connection with the preferred form of practicing it and modifications thereto, those of ordinary skill in the art will understand that many other modifications can be made to the present invention within the scope of the claims that follow. Accordingly, it is not intended that the scope of the invention in any way be limited by the above description, but instead be determined entirely by reference to the claims that follow.

The invention in which an exclusive right is claimed is defined by the following:

1. An illumination system adapted to increase an amount of light incident upon an object that is moving relative to the illumination system, comprising:

(a) a light source producing a beam of light;

(b) a first reflecting surface and a second reflecting surface disposed opposite each other and maintained in a facing relationship so as to define a reflection cavity, the first reflecting surface and the second reflecting surface being separated by a defined distance, said reflection cavity having a field of view through which the object passes between the first reflecting surface and the second reflecting surface, said beam of light being incident upon the first reflecting surface at an acute angle relative to a normal to the first reflecting surface, the angle and the distance being selected such that said beam of light is reflected back and forth between the first and second reflecting surfaces so as to cross the field of view a predefined number of times, said beam of light thus being incident on the object a plurality of times as the object traverses the field of view; and (c) a detector disposed such that light from the object is incident upon the detector, while said beam of light is not incident upon the detector.

2. The illumination system of claim 1, wherein the light source comprises a laser.

3. The illumination system of claim 2, wherein the laser comprises one of a continuous wave laser and a pulsed laser.

4. The illumination system of claim 1, wherein the object is entrained in a fluid that flows through the field of view.

5. The illumination system of claim 1, wherein the first and second reflecting surfaces comprise first and second reflective coatings disposed on a transparent substrate.

6. The illumination system of claim 1, wherein the angle at which the beam of light is incident on the first reflecting surface and the distance are selected such that the beam of light is caused to overlap itself as it intersects a path along which the object traverses the field of view, when the beam is reflected between the first reflecting surface and the second reflecting surface.

7. The illumination system of claim 1, wherein the angle at which the beam of light is incident on the first reflecting surface and the distance are selected such that the beam of light passes through the field of view without overlapping itself as it intersects a path along which the object traverses the field of view, when the beam is reflected between the first reflecting surface and the second reflecting surface.

8. The illumination system of claim 1, further including an aperture that is disposed along a path of the beam of light so as to reduce a cross section of the beam of light transmitted through the aperture such that a variation in light intensity across the beam of light that is transmitted through the aperture is reduced.

9. The illumination system of claim 1, wherein the first reflecting surface forms an acute non zero angle with the second reflecting surface, said acute non zero angle being selected so that the beam of light that is reflected back and forth between successively different points along the first reflecting surface and the second reflecting surface in a first direction eventually begins to reflect back and forth between successively different points along the first reflecting surface and the second reflecting surface in a second direction that is opposite to the first.

10. The illumination system of claim 1, wherein at least one of the first reflecting surface and the second reflecting surface is curved to focus the beam of light onto an axis along which the object moves through the reflection cavity, to reduce a spread of the beam of light where the beam of light illuminates the object.

11. The illumination system of claim 10, wherein said at least one of the first and the second reflecting surfaces is curved about one of a first axis that is generally aligned with a direction of travel of the object, and a second axis that is generally orthogonal to the direction of travel of the object through the reflection cavity.

12. The illumination system of claim 10, wherein said at least one of the first and the second reflecting surfaces is curved about both a first axis that is generally aligned with a direction of travel of the object, and a second axis that is generally orthogonal to the direction of travel of the object through the reflection cavity.

13. An illumination system adapted to increase an amount of light incident upon an object that is moving relative to the illumination system, comprising:

(a) a light source producing a beam of light; and (b) a first reflecting surface and a second reflecting surface separated by a defined distance and disposed opposite each other and maintained in a facing relationship so as to define a reflection cavity, said reflection cavity having a field of view through which the object passes between the first reflecting surface and the second reflecting surface, said first reflecting surface being disposed in a non parallel orientation with respect to said second reflecting surface, said beam of light being incident upon the first reflecting surface at an acute angle relative to a normal to the first reflecting surface, the distance and the angle being selected so that said beam of light is reflected back and forth between the first and second surfaces so as to cross the field of view a defined number of times, said beam of light being incident on the object a plurality of times as the object traverses the field of view.

14. An illumination system adapted to increase an amount of light incident upon an object that is moving relative to the illumination system, comprising:

(a) a light source producing a beam of light; and (b) a first reflecting surface and a second reflecting surface disposed opposite each other and separated by a defined distance, such that they are maintained in a facing relationship so as to define a reflection cavity having a field of view through which the object passes between the first reflecting surface and the second reflecting surface, at least one of said first and said second reflecting surfaces being curved so as to have an optical power greater than one, said beam of light being incident upon the first reflecting surface at an acute angle relative to a normal to the first reflecting surface, the angle and the distance being selected such that said beam of light is reflected back and forth between the first and second surfaces so as to cross the field of view a specified number of times, said beam of light being incident on the object as the object traverses the field of view and focused upon the object by said at least one of said first and second reflecting surfaces that is curved.

15. The illumination system of claim 14, wherein said at least one of the first and the second reflecting surfaces is curved about one of a first axis that is generally aligned with a direction of travel of the object, and a second axis that is generally orthogonal to the direction of travel of the object through the reflection cavity.

16. The illumination system of claim 14, wherein said at least one of the first and the second reflecting surfaces is curved about both a first axis that is generally aligned with a direction of travel of the object, and a second axis that is generally orthogonal to the direction of travel of the object through the reflection cavity.

17. An illumination system adapted to increase an amount of light incident upon an object that is moving relative to the illumination system, comprising:

(a) a light source producing a beam of light;

(b) a first reflecting surface and a second reflecting surface separated by a defined distance and disposed opposite each other in a facing relationship so as to define a reflection cavity, said reflection cavity having a field of view through which the object passes between the first reflecting surface and the second reflecting surface, said beam of light being incident upon the first reflecting surface at an acute angle relative to a normal to the first reflecting surface, said distance and said angle having been selected such that said beam of light is reflected back and forth between the first and second reflecting surfaces so as to cross the field of view a defined number of times, said beam of light thus being incident on the object a plurality of times as the object traverses the field of view, and (c) means for reflecting the beam of light exiting the reflecting cavity back along its path and into the reflection cavity, so that the beam of light is again reflected back and forth across the reflection cavity between the first reflecting surface and the second reflecting surface, traversing the reflection cavity a further defined number of times.

18. The illumination system of claim 17, wherein said means comprises a third reflecting surface that reflects the beam of light exiting the reflecting cavity back along its path and into the cavity.

* * * * *